United States Patent [19]

Kepley

[11] Patent Number: 5,370,602
[45] Date of Patent: Dec. 6, 1994

[54] PHACOEMULSIFICATION PROBE CIRCUIT WITH PULSE WIDTH MODULATING DRIVE

[75] Inventor: Kevin P. Kepley, Dellwood, Mo.

[73] Assignee: American Cyanamid Company, Stamford, Conn.

[21] Appl. No.: 99,084

[22] Filed: Jul. 29, 1993

Related U.S. Application Data

[63] Continuation-in-part of Ser. No. 940,980, Sep. 4, 1992.

[51] Int. Cl.$^5$ .............................. A61F 9/00; A61B 8/10
[52] U.S. Cl. ........................................ 601/2; 606/127; 606/128; 604/22
[58] Field of Search .................... 606/102, 127, 128; 604/22; 128/24 AA; 601/2

[56] References Cited

U.S. PATENT DOCUMENTS

| | | | |
|---|---|---|---|
| 3,693,613 | 9/1972 | Kelman | 128/24 A |
| 3,902,495 | 9/1975 | Weiss et al. | 128/276 |
| 3,990,452 | 11/1976 | Murry et al. | 128/305 |
| 4,378,530 | 3/1983 | Garde | 330/297 |
| 4,504,264 | 3/1985 | Kelman | 604/22 |
| 4,587,958 | 6/1986 | Noguchi et al. | 128/24 A |
| 4,793,345 | 12/1988 | Lehmer | 128/303 |
| 4,827,911 | 5/1989 | Broodwin et al. | 128/24 AA |
| 4,868,445 | 9/1989 | Wand | 310/316 |
| 4,933,843 | 6/1990 | Scheller et al. | 364/413 |
| 5,042,460 | 8/1991 | Sakurai et al. | 128/24 |
| 5,121,023 | 6/1992 | Abel | 310/316 |
| 5,151,085 | 9/1992 | Sakurai et al. | 604/22 |
| 5,220,272 | 6/1993 | Nelson | 323/282 |

OTHER PUBLICATIONS

P. J. Baxandall, B.Sc. English, Transistor Sine-Wave LC Oscillators Feb. 1960.

Primary Examiner—Lee S. Cohen
Assistant Examiner—Bua M. Green
Attorney, Agent, or Firm—Polster, Lieder, Woodruff & Lucchesi

[57] ABSTRACT

A drive for a phacoemulsification probe includes a drive circuit for supplying electrical power to the probe, circuitry for sensing the electrical power supplied by the drive circuit to the probe and for supplying electrical signals indicative of the magnitude of the electrical power supplied. A manually operable input device provides a signal indicative of the transducer power level desired by the user of the probe. A control circuit is responsive to the signal indicative of the desired transducer power level and to the signals indicative of the magnitude of the supplied electrical power for providing control signals to the drive circuit to control the power applied in an efficient manner. The drive circuit includes a voltage controlled oscillator, responsive to at least one of the control signals, connected to a class S amplifier. The output of the class S amplifier is filtered before application to the probe transducer. The drive circuit has high efficiency when compared to prior art probe drives.

14 Claims, 3 Drawing Sheets

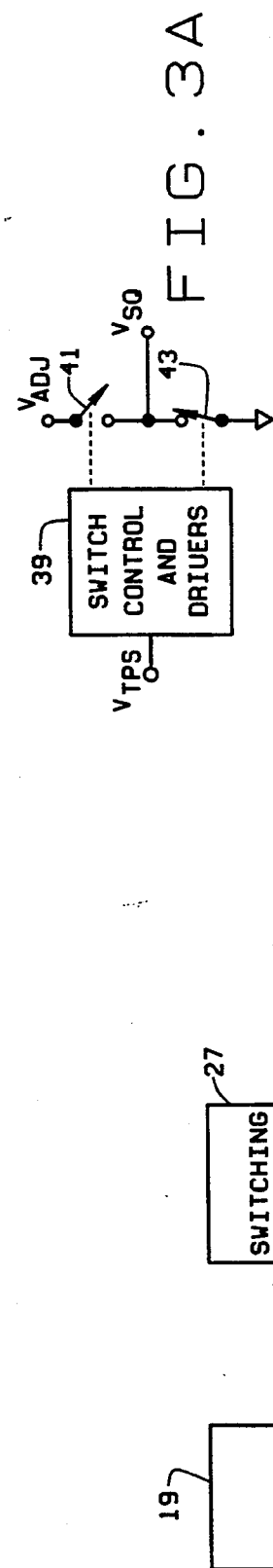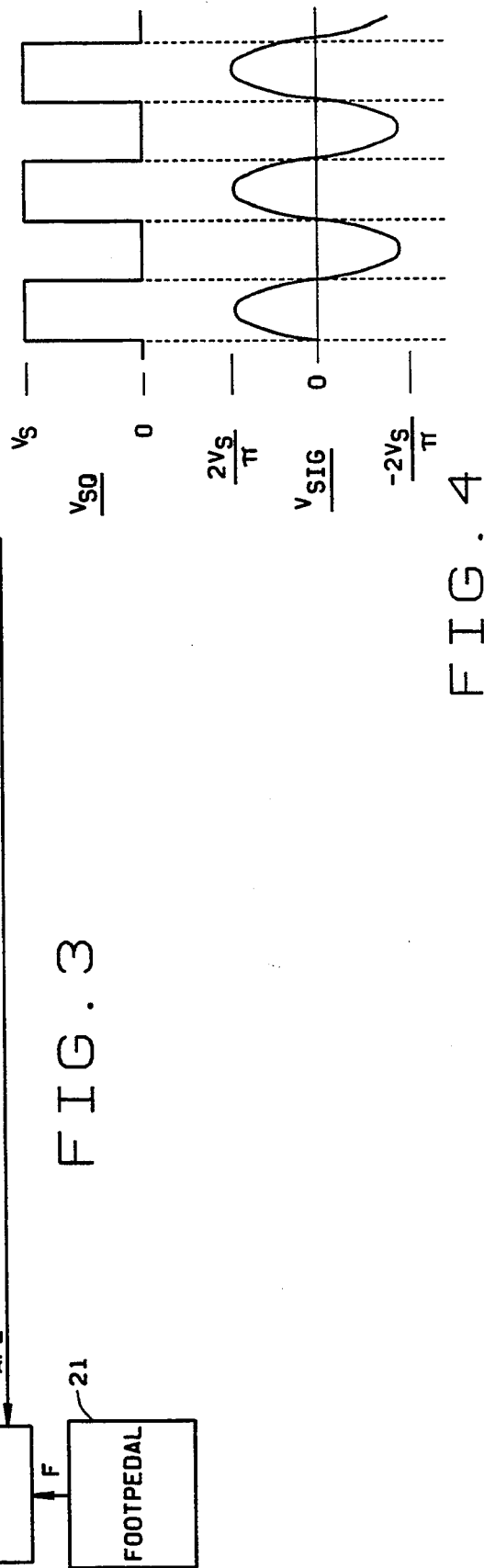
FIG. 3A
FIG. 3
FIG. 4

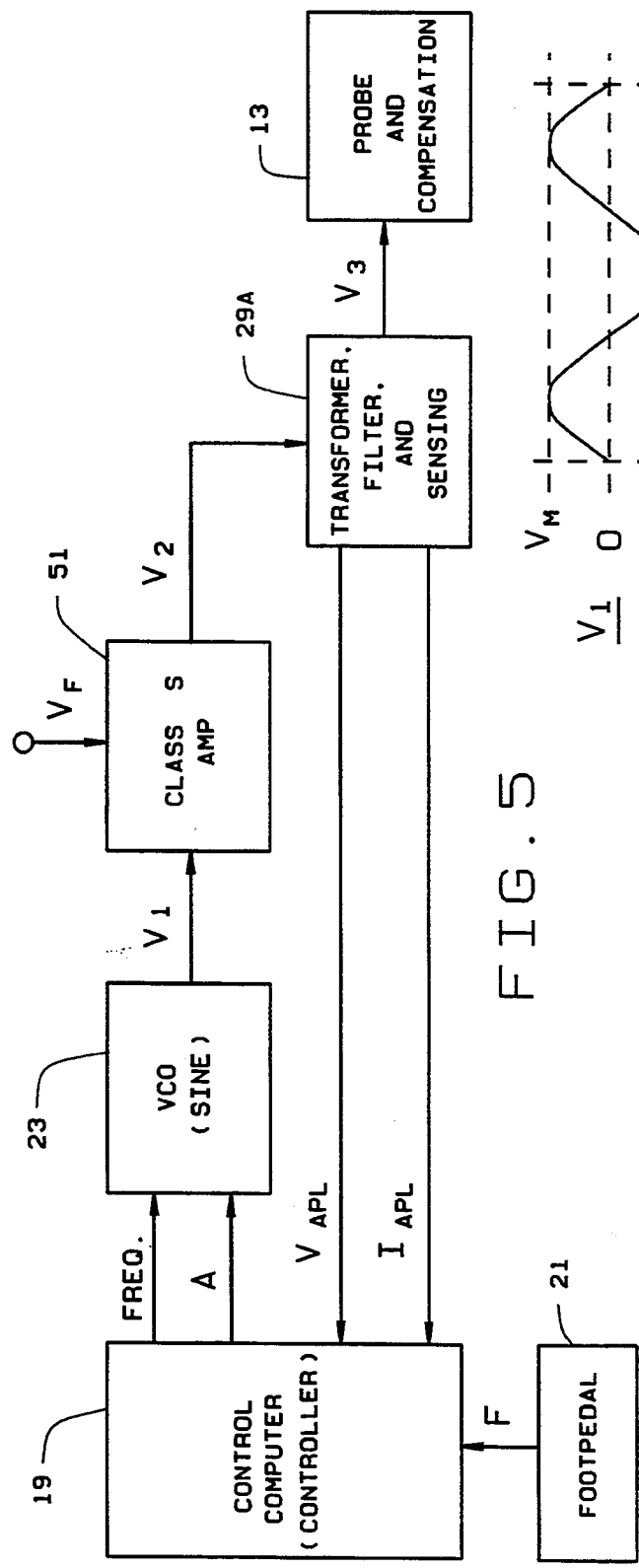
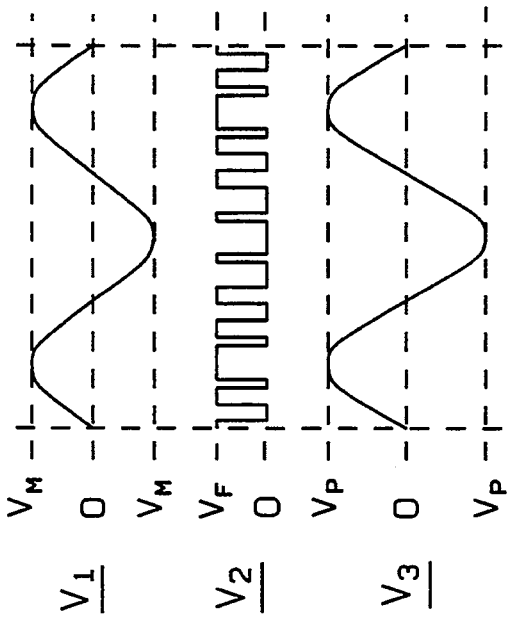
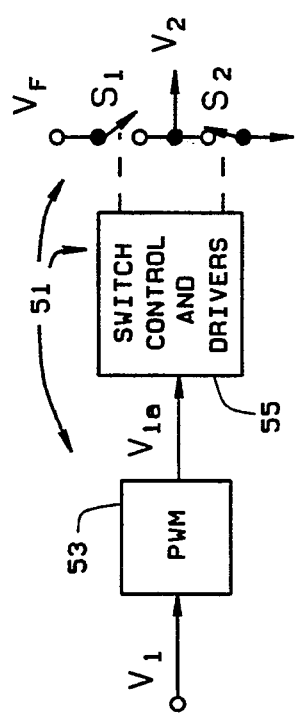

PHACOEMULSIFICATION PROBE CIRCUIT WITH PULSE WIDTH MODULATING DRIVE

CROSS-REFERENCE TO RELATED APPLICATION

This is a continuation-in-part application of copending application Ser. No. 07/940,980 filed Sep. 4, 1992.

BACKGROUND OF THE INVENTION

This invention relates to the field of phacoemulsification, and more particularly to drive circuits for phacoemulsification probes.

The use of ultrasonic handpieces or probes for the removal of cataracts in the human eye is well known. Typically, this procedure, called phacoemulsification, uses ultrasonic probes for rupturing cataracts in the eye, combined with aspiration of the resulting debris. Ultrasonic phacoemulsification probes conventionally include a piezoelectric crystal(s) affixed to a probe body. The crystal is driven by an electric power source and converts the electric power to ultrasonic power which is applied by the probe to the cataract.

The amount of power applied by the probe is a function of the frequency and amplitude of the driving electrical waveform and is typically under control of the surgeon using the probe. It is known that the frequency of the applied electrical waveform should be adjusted to the resonant frequency of the probe for efficient power conversion.

Prior art drive circuits for phacoemulsification probes function adequately, but they could be improved. For example, prior art drive circuits have a level of power consumption that is higher than desirable. This high level of power consumption is not only inefficient, it results in other deficiencies. Higher power consumption generates more heat, requiring the use of larger heat sinks than would be desirable, increasing the device's total weight and size, and, possibly, requiring additional cooling fans or other means of dissipating the excess heat.

SUMMARY OF THE INVENTION

Among the various objects and features of the present invention may be noted the provision of a phacoemulsification probe drive circuit with improved efficiency.

A second object is the provision of such a probe drive circuit with reduced power consumption.

A third object is the provision of such a probe drive circuit with reduced size and weight.

Other objects and features will be in part apparent and in part pointed out hereinafter.

Briefly, a phacoemulsification probe system of the present invention includes an ultrasonic handpiece having a distal end of a size suitable for insertion into a patient's eye for emulsifying cataracts and the like. The handpiece includes a transducer for converting electrical power to ultrasonic power for application to the patient. A drive circuit is provided for supplying electrical power to the ultrasonic handpiece transducer. Circuitry is included for sensing the electrical power supplied by the drive circuit to the ultrasonic handpiece transducer and for supplying electrical signals indicative of the magnitude of the electrical power supplied by the drive circuit. A manually operable input device is included for providing a signal indicative of the transducer power level desired by the user of the phacoemulsification probe system. A control circuit is responsive to the signal indicative of the desired transducer power level and to the signals indicative of the magnitude of the supplied electrical power for providing control signals to the drive circuit to control the power applied in an efficient manner. The drive circuit includes waveform generating circuitry responsive to at least one of the control signals to generate a corresponding pulse-width modulated waveform having a predetermined amplitude. Circuitry is also provided for filtering the pulse-width modulated waveform for application to the transducer, the shape of the pulse-width modulated waveform determining the amount of electrical power supplied to the transducer.

A method of the present invention involves driving a phacoemulsification apparatus having an ultrasonic handpiece with a distal end of a size suitable for insertion into a patient's eye for emulsifying cataracts and the like, which handpiece includes a transducer for converting electrical power to ultrasonic power for application to the patient, which apparatus also has a drive circuit connected to the ultrasonic handpiece transducer and a manually operable input device for signaling the desired transducer power level. The drive circuit includes a waveform generating circuit for applying power in a pulse-width modulated waveform. The method includes the steps of supplying electrical power from the drive circuit through a filtering circuit to the ultrasonic handpiece transducer, sensing the electrical power supplied to the ultrasonic handpiece transducer, comparing the electrical power supplied by the drive circuit with the desired transducer power level, and varying the amplitude of a sine-wave input to the waveform generating means to control the filtered power to efficiently supply the desired power to the transducer. The amplitude of the sine-wave input is varied to correspond to the desired output power selected by the manually operable input device.

BRIEF DESCRIPTION OF THE DRAWINGS

FIG. 3 is a block diagram of a second embodiment of the phacoemulsification probe system of the present invention;

FIG. 3A is a schematic of a portion of the circuitry of FIG. 3;

FIG. 4 is a diagram illustrating the square-wave output of a portion of the drive circuit of the system of FIG. 3;

FIG. 5 is a block diagram of a third embodiment of the phacoemulsification probe system of the present invention;

FIG. 5A is a schematic of a portion of the circuitry of FIG. 5; and

FIG. 6 is a diagram illustrating the waveforms of the drive circuit of the system of FIG. 5.

Similar reference characters indicate similar parts throughout the several views of the drawings.

DESCRIPTION OF THE PREFERRED EMBODIMENT

Figure 1:
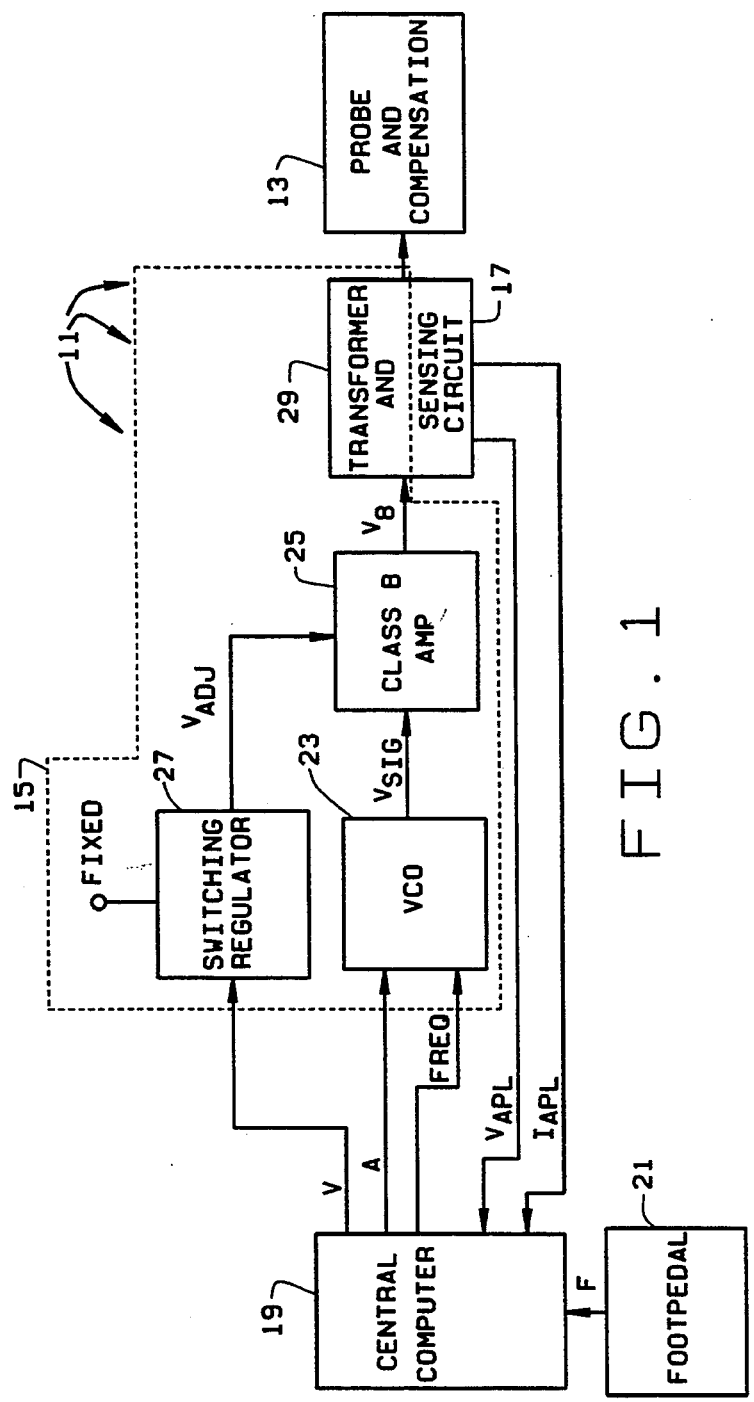
FIG. 1 is a block diagram of the phacoemulsification probe system of the present invention.

Turning to the drawings, a phacoemulsification probe system 11 of the present invention includes an ultrasonic handpiece or probe 13 having a distal end of a size suitable for insertion into a patient's eye for emulsifying cataracts and the like. For purposes of this invention, handpiece 13 may be of any conventional piezoelectric design and includes a conventional transducer for converting electrical power to ultrasonic power for application to the patient (not shown).

A drive circuit 15 is provided for supplying electrical power to the transducer of ultrasonic handpiece 13. The voltage (labelled VAPL on FIG. 1) and current (labelled IAPL) actually supplied by the drive circuit is sensed by conventional voltage and current sensing circuitry 17 and electrical signals representing the applied voltage VAPL and applied current are supplied from the sensing circuitry to a control computer 19. Control computer 19 may be a conventional microprocessor suitably programmed to perform the functions described herein.

In addition to inputs VAPL and IAPL, computer 19 receives an input (labelled F) from a manually operable input device 21. Input device 21 is a conventional footpedal by means of which the surgeon signals the computer to increase or decrease the output power of probe 13.

For purposes of this invention, control computer 19 has three output signals (labelled V, A, and "freq") which are provided to control drive circuit 15. It is known in the art to provide control signals A and "freq" to provide the output power at the desired level and at the resonant frequency of the probe. The present invention is not concerned with control signal "freq" which can be varied as taught in the prior art. Rather it deals with control signals A and V.

Control signals A and "freq" from the control computer are provided to a conventional voltage controlled oscillator 23 whose output is supplied to a class B amplifier 25. Power for the class B amplifier is obtained from a switching regulator 27, and the output of amplifier 25 is supplied to drive a transformer 29. The output of transformer 29 is applied to probe 13 and that same output is sensed by sensing circuit 17 as described above.

Switching regulator 27 provides a supply voltage (labelled VADJ) to amplifier 25 which is a function of the other control signal from computer 19, namely control signal V. In general control signal V is used to control the efficiency of the application of power, specifically to substantially minimize the amplifier's power consumption, while control signal A is used to control the level of power applied to the probe.

Operation of system 11 is as follows: During use of system 11 (after initial adjustment of control signal "freq" to find the resonant frequency of probe 13), control computer 19 receives signal F from footpedal 21, which signal represents the power level the user desires to be applied to probe 13. Computer 19 in response adjusts the amplitude control signal A to voltage controlled oscillator 23 to approximately supply the desired power level to the probe. The actual applied voltage and current VAPL and IAPL are sensed and signals representing them are supplied to computer 19 to close the control loop between the drive circuit and computer 19. The computer uses this information concerning the actual applied power to adjust control signal A as necessary to deliver the desired power corresponding to input signal F to the probe.

Although control of signal A results in the desired power being applied to the probe, it exerts no control over the efficiency of drive circuit 15. To control that efficiency, and thereby substantially minimize the power consumption, computer 19 further adjusts control signal V to switching regulator 27. The switching regulator (preferably a boost regulator, although other types of switching regulators could also be used) is provided with a fixed voltage (labelled VFIXED) which it regulates as commanded by control signal V. Adjustment of control signal V causes the supply voltage output VADJ of the switching regulator to change in a controlled manner.

Figure 2:
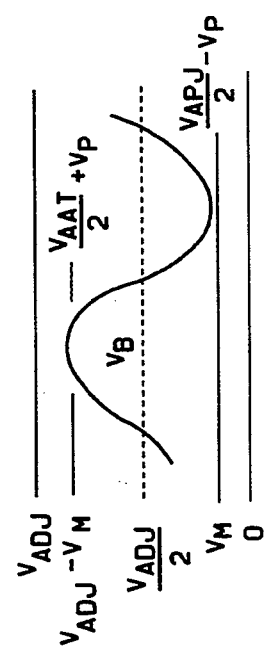
FIG. 2 is a diagram illustrating the voltage levels involved in the system of FIG. 1.

The value of supply voltage VADJ is determined as follows: Referring to FIG. 2, the voltage VB is the signal applied to transformer 29. That signal is a sine wave of amplitude VP. Thus, voltage VB has a peak to peak amplitude of 2*VP. Class B amplifier 25 works in such a way that VB=VADJ/2+VP* sin wt. Computer 19 controls switching regulator 27 so that the supply voltage VADJ remains at the level VADJ=2*VP+2*VM, as VP varies in response to footpedal signal F. VM is the marginal voltage required by the class B amplifier so that the signal is properly passed without significant distortion. If VADJ were larger than this value (2*(VP+VM)), then excess power would be dissipated in amplifier 25. If VADJ were less than this value, then the signal would be distorted.

Turning to FIG. 3, the second embodiment of the present invention is similar to the first, but instead of a class B amplifier 25 it has a totem pole switch 31, followed by a shaping filter 33. In the same manner as the system of FIG. 1, the control computer 19 receives a signal F from the footpedal 21 representing the desired power level to be applied to the probe 13. The control computer then adjusts the amplitude signal A to the switching regulator 27 which controls the magnitude of the supply voltage Vs. The value of Vs in turn determines the amplitude of the square wave Vsq applied to shaping filter 33. The shaping filter (normally a bandpass filter) rejects the harmonics of the square wave (and any DC level) and passes only the fundamental frequency. Output Vsig is thus a sinusoidal signal which is applied to the transformer and sensing circuit 29. Circuit 29 senses the applied voltage and current to the probe, namely Vapl and Iapl. From these signals, the actual power applied to the probe is calculated by the control computer. This allows the control computer to close the control loop and control signal A to deliver the desired power commanded by signal F to the probe.

It should again be understood that the frequency, controlled by signal "freq," is adjusted once at the beginning of the operation to find the resonant frequency of the probe, and then left constant thereafter. Changes in the desired power are made by changing control signal "A."

Turning to FIG. 3A it can be seen that the output from VCO 23 is supplied to the switch control and driver portion 39 of totem-pole switch 31, which in turn open and close switches 41 and 43 to provide the square-wave output shown on the top line of FIG. 4. This square-wave is filtered by shaping filter 33 to provide the sinusoidal waveform Vsig shown on the bottom line of FIG. 4 to the transformer.

Turning to FIGS. 5, 5A and 6, the third embodiment of the present invention also has a control computer 19. (Although shown as a computer, circuit 19 could be a controller instead.) Computer or controller 19 receives a signal F from footpedal manually operated input device 21, which signal represents the desired power level to be applied to the probe 13. The computer initially adjusts a control signal "freq" at the beginning of the operation to find the resonant frequency of probe 13, and then leaves the "freq" signal constant thereafter.

It then adjusts a second control signal, an amplitude control signal "A", so that the applied power is the same as the desired power. Computer 19 controls the power using the amplitude control signal "A" in a continuous closed loop manner, similar to that described in connection with the first and second embodiments. The applied power is computed by computer 19 from sensed signals Vapl and Iapl from the transformer, filter and sensing circuitry 29A.

The amplitude control signal "A" is supplied by computer 19 to voltage controlled oscillator (VCO) 23, which in response outputs a sine wave at an amplitude proportional to signal "A" and at a frequency proportional to the control signal "freq." This sine wave signal, labelled V1 in FIGS. 5 and 6, is applied to a class S amplifier 51. Class S amplifier 51 applies a pulse-width modulated square wave, labelled V2 in FIGS. 5 and 6, to the transformer, filter, and sensing circuitry 29A. The filter portion of this circuitry filters out the switching frequency component of signal V2, leaving the sine wave at the desired amplitude. This signal passes through circuitry 29A and is applied to probe 13 as signal V3 (see FIGS. 5 and 6).

Turning to FIG. 5A, class S amplifier 51 includes a pulse width modulator (PWM) circuit 53 which takes the sinusoidal input signal V1 from VCO 23 and converts it to a pulse width modulated signal V1a. Signal V1a switches at many times the bandwidth of signal V1 from the VCO. Signal V1a in turn causes Switch Control and Driver circuitry 55 to alternately switch a pair of totem pole switches S1 and S2. This produces a square wave, pulse width modulated signal which is signal V2. Signal V2 has a fixed amplitude Vf corresponding to the supply voltage, but a waveform shape which varies depending upon the desired applied power. Of course, positive and negative voltages could be used to supply totem pole switch (S1 and S2), but this would complicate the design of the switch control and driver circuitry 55.

It should be appreciated that the particular design of class S amplifier 51 could be varied as desired. Amplifiers of this class are described in "Solid State Radio Engineering", by Krauss, Bastian and Raab (Wiley 1980) at pp. 458ff, the disclosure of which is hereby incorporated herein by reference.

It has been found that the systems of the present invention provide greatly increased efficiencies over those of the prior art. For example, with a prior art system, the supply voltage Vs is fixed at some value which is large enough so that the maximum power can be delivered to the load with the largest load resistance. For comparison purposes, assume that all three systems (prior art, FIG. 1, and FIG. 3) are designed to deliver a maximum power of 20W to a load in the range of 2.2 ohm to 11.1 ohm.

The prior art system must have a supply voltage of 48V in order to be able to deliver maximum power (20W) to the largest resistive load (11.1 ohm). For comparison, the power dissipated in the prior art system is calculated to vary from 8.9W at 11.1 ohm (68.7% efficiency) up to 45.1W at 2.2 ohm (30.7% efficiency). In contrast the system of FIG. 1 has a power dissipation identical to that of the prior art system at 11.1 ohm, but a power dissipation of only 13.6W (59.6% efficiency) at 2.2 ohms. This is almost double the efficiency of the prior art system at low resistance. Even at average load resistance (approximately 4 ohm), the system of FIG. 1 is approximately 20% more efficient than the prior art system.

The system of FIG. 3 is even more efficient. The efficiency varies from about 95% to 99% as the load resistance varies from 2.2 to 11.1 ohms. This is a very significant improvement. The maximum dissipation that must be handled with the system of FIG. 3 is less than a watt. At this level of dissipation, in some applications it may be possible to eliminate a heat sink altogether. The system of FIG. 5 in practice is found to have efficiencies similar to those of the system of FIG. 3.

Although the efficiencies mentioned above are theoretical, in practice they can be closely approached, giving the systems great practical advantages over the prior art. In addition, it should be noted that the efficiencies mentioned above relate to only the amplifier and not to any efficiencies resulting from the use of other components.

It should be realized that the components described above are illustrative only. Any number of similar components could be used with the same invention. Numerous variations of the present constructions and methods may be used. The examples given herein are merely illustrative, and are not to be construed in a limiting sense.

What is claimed is:

1. A phacoemulsification probe system comprising:
   an ultrasonic handpiece having a distal end of a size suitable for insertion into a patient's eye for emulsifying cataracts, said handpiece including a transducer for converting electrical power to ultrasonic power for application to the patient;
   drive circuit means for supplying electrical power to the ultrasonic handpiece transducer;
   means for sensing the electrical power supplied by the drive circuit means to the ultrasonic handpiece transducer and for supplying electrical signals indicative of a magnitude of said electrical power supplied by the drive circuit means;
   manually operable input means for providing a signal indicative of a transducer power level desired by a user of the phacoemulsification probe system; and
   control circuit means responsive to the signal indicative of the desired transducer power level and to the signals indicative of the magnitude of the supplied electrical power for providing control signals to the drive circuit means to control the power applied;
   said drive circuit means including waveform generating means responsive to at least one of the control signals to generate a corresponding pulse-width modulated waveform having a predetermined amplitude, and means for filtering the pulse-width modulated waveform for application to the transducer, the shape of the pulse-width modulated waveform determining the amount of electrical power supplied to the transducer.

2. The phacoemulsification probe system as set forth in claim 1 wherein the waveform generating means includes a class S amplifier, a output of the class S amplifier being said pulse-width modulated waveform.

3. The phacoemulsification probe system as set forth in claim 2 wherein the waveform generating means further includes a voltage controlled oscillator responsive to one of said control signals to supply a sine-wave waveform at an amplitude determined by said control signal to the class S amplifier.

4. The phacoemulsification probe system as set forth in claim 3 wherein the class S amplifier provides a different pulse-width modulated waveform for each value of amplitude of the sine-wave waveform from the voltage controlled oscillator.

5. The phacoemulsification probe system as set forth in claim 3 wherein the class S amplifier includes a pulse width modulator circuit.

6. The phacoemulsification probe system as set forth in claim 5 wherein the pulse-width modulator circuit has an output bandwidth many times a bandwidth of the voltage controlled oscillator.

7. The phacoemulsification probe system as set forth in claim 6 wherein the class S amplifier includes a totem-pole switch.

8. The phacoemulsification probe system as set forth in claim 7 wherein the totem pole switch is switched at a frequency substantially higher than an output frequency of the voltage controlled oscillator.

9. A method of driving a phacoemulsification apparatus having an ultrasonic handpiece with a distal end of a size suitable for insertion into a patient's eye for emulsifying cataracts, said handpiece including a transducer for converting electrical power to ultrasonic power for application to the patient, said apparatus also having a drive circuit connected to the ultrasonic handpiece transducer and also having a manually operable input device for signaling the desired transducer power level, said drive circuit including waveform generating means for applying power in a pulse-width modulated waveform, said method comprising:

supplying electrical power from the drive circuit through a filtering circuit to the ultrasonic handpiece transducer;

sensing the electrical power supplied to the ultrasonic handpiece transducer;

comparing the electrical power supplied by the drive circuit with a desired transducer power level; and varying the amplitude of a sine-wave input to the waveform generating means to control the filtered power to supply power to the transducer, said amplitude of the sine-wave input being varied to correspond to the desired output power selected by the manually operable input device.

10. The method as set forth in claim 9 wherein the power supplying step includes supplying said sine-wave input to a class S amplifier.

11. The method as set forth in claim 10 wherein the class S amplifier generates the pulse-width modulated waveform whose shape is determined by the amplitude and frequency of said sine-wave input, further including the step of fixing said frequency of the sine-wave input to correspond to a resonant frequency of the ultrasonic handpiece and thereafter varying the power applied by varying the amplitude of the sine-wave input.

12. A phacoemulsification probe system comprising:

an ultrasonic handpiece having a distal end of a size suitable for insertion into a patient's eye for emulsifying cataracts, said handpiece including a transducer for converting electrical power to ultrasonic power for application to the patient;

drive circuit means for supplying electrical power to the ultrasonic handpiece transducer;

means for sensing the electrical power supplied by the drive circuit means to the ultrasonic handpiece transducer and for supplying electrical signals indicative of a magnitude of said electrical power supplied by the drive circuit means;

manually operable input means for providing a signal indicative of a transducer power level desired by a user of the phacoemulsification probe system; and control circuit means responsive to the signal indicative of the desired transducer power level and to the signals indicative of the magnitude of the supplied electrical power for providing control signals to the drive circuit means to control the power applied;

said drive circuit means including waveform generating means responsive to at least one of the control signals to generate a corresponding pulse-width modulated waveform having a predetermined amplitude, said means including a class S amplifier, an output of the class S amplifier being said pulse-width modulated waveform, and a voltage controlled oscillator responsive to one of said control signals to supply a sine-wave waveform at an amplitude determined by said control signal to the class S amplifier;

the class S amplifier providing a different pulse-width modulated waveform for each value of amplitude of the sine-wave waveform from the voltage controlled oscillator;

the class S amplifier including a pulse width modulator circuit, the pulse width modulator circuit has an output bandwidth many times the bandwidth of the voltage controlled oscillator, and means for filtering the pulse-width modulated waveform for application to the transducer, the shape of the pulse-width modulated waveform determining the amount of electrical power supplied to the transducer.

13. The phacoemulsification probe system as set forth in claim 12 wherein the totem pole switch is switched at a frequency substantially higher than an output frequency of the voltage controlled oscillator.

14. A method of driving a phacoemulsification apparatus having an ultrasonic handpiece with a distal end of a size suitable for insertion into a patient's eye for emulsifying cataracts, said handpiece including a transducer for converting electrical power to ultrasonic power for application to the patient, said apparatus also having a drive circuit connected to the ultrasonic handpiece transducer and also having a manually operable input device for signaling the desired transducer power level, said drive circuit including waveform generating means for applying power in a pulse-width modulated waveform, said method comprising:

supplying electrical power from the drive circuit as a sine-wave input to a class S amplifier to the ultrasonic handpiece transducer wherein the class S amplifier generates a pulse-width modulated waveform whose shape is determined by the amplitude and frequency the said sine-wave input;

sensing the electrical power supplied to the ultrasonic handpiece transducer;

comparing the electrical power supplied by the drive circuit with a desired transducer power level;

varying the amplitude of the sine-wave input to the waveform generating means to control the filtered power to supply power to the transducer, said amplitude of the sine-wave input being varied to correspond to the desired output power selected by the manually operable input device, and fixing said frequency of the sine-wave input to correspond to the resonant frequency of the probe and thereafter varying the power applied by varying the amplitude of the sine-wave input.

* * * * *